United States Patent
Migneco et al.

(10) Patent No.: US 11,052,223 B2
(45) Date of Patent: Jul. 6, 2021

(54) SEAT ASSEMBLY AND METHOD

(71) Applicant: Lear Corporation, Southfield, MI (US)

(72) Inventors: Francesco Migneco, Saline, MI (US);
Sajad Arabnejad, Ann Arbor, MI (US);
David Gallagher, Sterling Heights, MI (US)

(73) Assignee: Lear Corporation, Southfield, MI (US)

( * ) Notice: Subject to any disclaimer, the term of this patent is extended or adjusted under 35 U.S.C. 154(b) by 33 days.

(21) Appl. No.: 16/523,102

(22) Filed: Jul. 26, 2019

(65) Prior Publication Data

US 2019/0344043 A1   Nov. 14, 2019

Related U.S. Application Data

(63) Continuation-in-part of application No. 15/851,003, filed on Dec. 21, 2017, now Pat. No. 10,569,668.

(51) Int. Cl.
*A61M 21/02*  (2006.01)
*B60N 2/02*  (2006.01)
(Continued)

(52) U.S. Cl.
CPC ........... *A61M 21/02* (2013.01); *A61B 5/0205* (2013.01); *A61B 5/168* (2013.01); *A61B 5/6893* (2013.01);
(Continued)

(58) Field of Classification Search
CPC .......... A61M 21/02; A61M 2205/3368; A61M 2021/0022; A61M 2021/0027; A61M 2021/0066; A61M 2230/42; A61M 2230/06; A61M 2205/3592; A61M 2205/3553; A61M 2205/70; A61M 2205/52; A61M 2205/609;
(Continued)

(56) References Cited

U.S. PATENT DOCUMENTS 5,769,490 A    6/1998  Falzon
6,056,360 A    5/2000  Schneider
(Continued)

FOREIGN PATENT DOCUMENTS

CN       2855822 Y    1/2007
CN     203186154 U    9/2013
(Continued)

OTHER PUBLICATIONS

Co-pending U.S. Appl. No. 16/821,128, filed Mar. 17, 2020.
(Continued)

*Primary Examiner* — Thomas Ingram
(74) *Attorney, Agent, or Firm* — Fishman Stewart PLLC

(57) ABSTRACT

A seat assembly includes a seat having a seat base and a seat back, an electronic control unit (ECU), a sensor assembly, and/or a response assembly. The ECU may be configured to determine via the sensor assembly whether an occupant disposed in the seat is in a first state, a second state, or a third state. The ECU may be configured to control the response assembly to change the state of said occupant from the first state to the second state and from the third state to the second state. The ECU may be configured to determine at least one of a breathing rate, a heart rate, and a heart rate variability of said occupant via the sensor assembly.

20 Claims, 6 Drawing Sheets

(51) Int. Cl.
| | |
|---|---|
| *B60N 2/90* | (2018.01) |
| *B60N 2/56* | (2006.01) |
| *A61B 5/00* | (2006.01) |
| *A61B 5/0205* | (2006.01) |
| *A61B 5/16* | (2006.01) |
| *B60N 2/00* | (2006.01) |
| *A61B 5/024* | (2006.01) |
| *A61B 5/08* | (2006.01) |
| *A61M 21/00* | (2006.01) |

(52) U.S. Cl.
CPC .......... *A61B 5/7405* (2013.01); *A61B 5/7455* (2013.01); *B60N 2/002* (2013.01); *B60N 2/0244* (2013.01); *B60N 2/56* (2013.01); *B60N 2/976* (2018.02); *A61B 5/02405* (2013.01); *A61B 5/0816* (2013.01); *A61M 2021/0022* (2013.01); *A61M 2021/0027* (2013.01); *A61M 2021/0066* (2013.01); *A61M 2205/3368* (2013.01); *A61M 2230/06* (2013.01); *A61M 2230/42* (2013.01); *B60N 2002/026* (2013.01); *B60N 2002/0268* (2013.01); *B60N 2002/981* (2018.02)

(58) Field of Classification Search
CPC .......... A61M 2230/63; A61M 2230/04; A61M 21/00; A61H 23/02; A61H 9/0078; A61H 2205/081; A61H 2201/5048; A61H 2201/507; A61H 2201/0207; A61H 2203/0431; A61H 2201/1633; A61H 2230/06; A61H 2230/42; A61H 2201/5058; B60N 2/0244; B60N 2/976; B60N 2/56; B60N 2/002; B60N 2002/026; B60N 2002/981; B60N 2002/0268; A61B 5/7455; A61B 2/6893; A61B 5/0205; A61B 5/02405; A61B 5/0816

See application file for complete search history.

(56) References Cited

U.S. PATENT DOCUMENTS

| | | | |
|---|---|---|---|
| 6,088,642 | A | 7/2000 | Finkelstein et al. |
| 6,088,643 | A | 7/2000 | Long et al. |
| 6,098,000 | A | 8/2000 | Long et al. |
| 6,345,839 | B1 | 2/2002 | Kuboki et al. |
| 6,353,207 | B1 | 3/2002 | Burt |
| 6,506,153 | B1 | 1/2003 | Littek et al. |
| 6,559,422 | B2 | 5/2003 | Burt |
| 6,682,494 | B1 | 1/2004 | Sleichter, III et al. |
| 6,908,152 | B2 | 6/2005 | McMillen |
| 7,011,369 | B2 | 3/2006 | Massara et al. |
| 7,083,232 | B2 | 8/2006 | Frank |
| 7,083,233 | B2 | 8/2006 | Massara et al. |
| 7,152,920 | B2 | 12/2006 | Sugiyama et al. |
| 7,201,446 | B2 | 4/2007 | Massara et al. |
| 7,219,923 | B2 | 5/2007 | Fujita et al. |
| 7,267,652 | B2 | 9/2007 | Coyle et al. |
| 7,303,231 | B2 | 12/2007 | Frank |
| 7,314,451 | B2 | 1/2008 | Halperin et al. |
| 7,417,536 | B2 | 8/2008 | Lakshmanan et al. |
| 7,731,279 | B2 | 6/2010 | Asada et al. |
| 7,808,395 | B2 | 10/2010 | Raisanen et al. |
| 7,862,119 | B2 | 1/2011 | Schafer et al. |
| 7,866,755 | B2 | 1/2011 | Okano |
| 7,900,736 | B2 | 3/2011 | Breed |
| 7,967,379 | B2 | 6/2011 | Walters et al. |
| 7,967,381 | B2 | 6/2011 | Sugiyama |
| 8,341,786 | B2 | 1/2013 | Oexman et al. |
| 8,444,558 | B2 | 5/2013 | Young et al. |
| 8,616,654 | B2 | 12/2013 | Zenk et al. |
| 8,706,204 | B2 | 4/2014 | Seo et al. |
| 8,710,784 | B2 | 4/2014 | Meyer et al. |
| 8,725,311 | B1* | 5/2014 | Breed .................. A61B 5/0507 701/1 |
| 8,794,707 | B2 | 8/2014 | Bocsanyi et al. |
| 8,958,955 | B2 | 2/2015 | Hotary et al. |
| 8,971,839 | B2 | 3/2015 | Hong |
| 8,979,191 | B2 | 3/2015 | Friderich et al. |
| 8,989,697 | B2 | 3/2015 | Leung et al. |
| 9,237,242 | B2 | 1/2016 | Basir |
| 9,272,689 | B2* | 3/2016 | Fung ........................ G07C 9/37 |
| 9,277,385 | B2 | 3/2016 | Iwamoto |
| 9,504,416 | B2 | 11/2016 | Young et al. |
| 9,815,385 | B2 | 11/2017 | Lippman et al. |
| 9,883,821 | B2 | 2/2018 | Muehlsteff |
| 9,980,680 | B2 | 5/2018 | Matsumoto |
| 10,034,631 | B1* | 7/2018 | Gallagher ............ A61B 5/6893 |
| 10,210,409 | B1 | 2/2019 | Migneco et al. |
| 10,213,147 | B2 | 2/2019 | Gallagher et al. |
| 10,328,823 | B2 | 6/2019 | O'Bannon et al. |
| 10,358,065 | B2 | 7/2019 | McMillen et al. |
| 10,369,074 | B2 | 8/2019 | Oberg et al. |
| 10,379,535 | B2 | 8/2019 | Migneco et al. |
| 10,470,968 | B2 | 11/2019 | Saren et al. |
| 10,471,868 | B2 | 11/2019 | Wheeler |
| 10,492,979 | B2 | 12/2019 | Norman et al. |
| 10,556,532 | B2 | 2/2020 | Gallagher et al. |
| 10,569,668 | B2 | 2/2020 | Migneco et al. |
| 10,576,855 | B2 | 3/2020 | Dorfler et al. |
| 10,640,010 | B2 | 5/2020 | Yetukuri et al. |
| 10,709,386 | B2 | 7/2020 | Gallagher et al. |
| 10,807,439 | B2 | 10/2020 | Migneco et al. |
| 2003/0075959 | A1 | 4/2003 | Xue et al. |
| 2004/0119599 | A1 | 6/2004 | Stevenson et al. |
| 2007/0118054 | A1 | 5/2007 | Pinhas et al. |
| 2008/0255731 | A1 | 10/2008 | Mita et al. |
| 2008/0267460 | A1 | 10/2008 | Aoki et al. |
| 2009/0008970 | A1 | 1/2009 | Flory et al. |
| 2009/0030578 | A1 | 1/2009 | Periot et al. |
| 2010/0087748 | A1 | 4/2010 | Tobola et al. |
| 2011/0015468 | A1* | 1/2011 | Aarts .................. A61B 5/02405 600/26 |
| 2012/0086249 | A1 | 4/2012 | Hotary et al. |
| 2013/0090816 | A1 | 4/2013 | Huber |
| 2013/0251216 | A1 | 9/2013 | Smowton et al. |
| 2014/0207333 | A1 | 7/2014 | Vandivier et al. |
| 2014/0319895 | A1 | 10/2014 | Lange-Mao et al. |
| 2014/0361871 | A1 | 12/2014 | Silva et al. |
| 2015/0084985 | A1 | 3/2015 | Baudu |
| 2015/0266405 | A1 | 9/2015 | Fitzpatrick et al. |
| 2015/0313475 | A1* | 11/2015 | Benson ................ A61B 5/0245 297/217.3 |
| 2015/0351692 | A1 | 12/2015 | Pereny et al. |
| 2015/0352979 | A1 | 12/2015 | O'Bannon et al. |
| 2015/0352990 | A1 | 12/2015 | Zouzal et al. |
| 2016/0001781 | A1* | 1/2016 | Fung ........................ G16H 50/20 701/36 |
| 2016/0143803 | A1 | 5/2016 | Portales |
| 2016/0250956 | A1 | 9/2016 | Seiting et al. |
| 2016/0278729 | A1 | 9/2016 | Ridao Granado et al. |
| 2017/0043681 | A1* | 2/2017 | Seiller .................... B60N 2/914 |
| 2017/0086588 | A1 | 3/2017 | Patrick et al. |
| 2017/0274906 | A1 | 9/2017 | Hassan et al. |
| 2017/0361748 | A1 | 12/2017 | Meachum et al. |
| 2018/0008507 | A1 | 1/2018 | Saren et al. |
| 2018/0009343 | A1 | 1/2018 | Saren et al. |
| 2018/0325264 | A1 | 11/2018 | Gallagher et al. |
| 2018/0345833 | A1 | 12/2018 | Gallagher et al. |
| 2019/0053761 | A1 | 2/2019 | Young et al. |
| 2019/0054796 | A1 | 2/2019 | Thomas |
| 2019/0126036 | A1 | 5/2019 | Franco-Obregon et al. |
| 2019/0133511 | A1 | 5/2019 | Migneco et al. |
| 2019/0168771 | A1 | 6/2019 | Migneco et al. |
| 2019/0193591 | A1 | 6/2019 | Migneco et al. |
| 2019/0239815 | A1 | 8/2019 | Gallagher et al. |
| 2019/0275860 | A1 | 9/2019 | Migneco et al. |
| 2019/0332902 | A1 | 10/2019 | Gallagher et al. |
| 2019/0337431 | A1 | 11/2019 | McMillen et al. |
| 2020/0035237 | A1 | 1/2020 | Kim et al. |
| 2020/0170576 | A1 | 6/2020 | Lerner |

(56) References Cited

U.S. PATENT DOCUMENTS

| | | |
|---|---|---|
| 2020/0188211 A1 | 6/2020 | Ellermann |
| 2020/0231428 A1 | 7/2020 | Migneco et al. |
| 2020/0253381 A1 | 8/2020 | Dorfler et al. |

FOREIGN PATENT DOCUMENTS

| | | | |
|---|---|---|---|
| CN | 104252615 | A | 12/2014 |
| CN | 205468657 | U | 8/2016 |
| DE | 10027686 | A1 | 1/2002 |
| DE | 10063478 | A1 | 7/2002 |
| DE | 102004010626 | A1 | 6/2005 |
| DE | 102004013674 | A1 | 10/2005 |
| DE | 102006029871 | A1 | 1/2008 |
| DE | 102008029339 | A1 | 1/2009 |
| DE | 102009008421 | A1 | 10/2009 |
| DE | 102009035566 | A1 | 2/2010 |
| DE | 102009031331 | A1 | 8/2010 |
| DE | 102009033041 | A1 | 1/2011 |
| DE | 102010021332 | A1 | 1/2011 |
| DE | 102010049152 | A1 | 11/2011 |
| DE | 102011012431 | A1 | 11/2011 |
| DE | 102011016073 | A1 | 12/2011 |
| DE | 102011017238 | A1 | 12/2011 |
| DE | 102011102021 | A1 | 11/2012 |
| DE | 102011113100 | A1 | 3/2013 |
| DE | 102011116194 | A1 | 4/2013 |
| DE | 102012201430 | A1 | 4/2013 |
| DE | 102012216869 | A1 | 3/2014 |
| DE | 202015104103 | U1 | 8/2015 |
| DE | 102014002942 | A1 | 9/2015 |
| DE | 102015011460 | A1 | 3/2016 |
| DE | 102015011461 | A1 | 3/2016 |
| DE | 102017110812 | A1 | 1/2018 |
| DE | 102016011481 | A1 | 3/2018 |
| DE | 202017103162 | U1 | 5/2018 |
| DE | 102018000765 | A1 | 8/2019 |
| DE | 102018001230 | A1 | 8/2019 |
| DE | 202019100400 | U1 | 1/2020 |
| DE | 202019100710 | U1 | 2/2020 |
| DE | 102018007921 | A1 | 4/2020 |
| DE | 202019102879 | U1 | 5/2020 |
| DE | 202019105369 | U1 | 5/2020 |
| DE | 102019008724 | A1 | 8/2020 |
| EP | 1077154 | A2 | 2/2001 |
| EP | 1749477 | A1 | 2/2007 |
| EP | 1932715 | A1 | 6/2008 |
| EP | 2149475 | A1 | 2/2010 |
| EP | 2205460 | B1 | 3/2016 |
| FR | 2988654 | A1 | 10/2013 |
| GB | 2512136 | A | 9/2014 |
| JP | 2001269380 | A | 10/2001 |
| JP | 2005137896 | A | 6/2005 |
| JP | 2005237456 | A | 9/2005 |
| JP | 2006014756 | A | 1/2006 |
| JP | 3857869 | B2 | 12/2006 |
| JP | 2009172145 | A | 8/2009 |
| JP | 2012196253 | A | 10/2012 |
| JP | 2013163405 | A | 8/2013 |
| JP | 2019131049 | A | 8/2019 |
| WO | 2011144280 | A1 | 11/2011 |
| WO | 2012039368 | | 3/2012 |
| WO | 2013144498 | A1 | 10/2013 |
| WO | 2015127193 | A1 | 8/2015 |
| WO | 2016099299 | A1 | 6/2016 |

OTHER PUBLICATIONS

Co-pending U.S. Appl. No. 15/930,777, filed May 13, 2020.
Co-pending U.S. Appl. No. 15/930,802, filed May 13, 2020.
Co-pending U.S. Appl. No. 15/930,835, filed May 13, 2020.
Co-pending U.S. Appl. No. 15/930,865, filed May 13, 2020.
Co-pending U.S. Appl. No. 17/109,652, filed Dec. 2, 2020.

* cited by examiner

SEAT ASSEMBLY AND METHOD

CROSS-REFERENCE TO RELATED APPLICATION

This application is a continuation-in-part application of U.S. patent application Ser. No. 15/851,003, filed on Dec. 21, 2017, the disclosure of which is hereby incorporated by reference in its entirety as though fully set forth herein.

TECHNICAL FIELD

The present disclosure generally relates to seat assemblies and methods, including seat assemblies and methods that may be used in connection with a vehicle, such as an automobile.

BACKGROUND

This background description is set forth below for the purpose of providing context only. Therefore, any aspect of this background description, to the extent that it does not otherwise qualify as prior art, is neither expressly nor impliedly admitted as prior art against the instant disclosure.

Some seat assemblies may not include sufficient functionality or features, and/or may not be configured for altering a state (e.g., a physical state) of an occupant or automatically altering the state of an occupant.

There is a desire for solutions/options that minimize or eliminate one or more challenges or shortcomings of seat assemblies. The foregoing discussion is intended only to illustrate examples of the present field and are not a disavowal of scope.

SUMMARY

In embodiments, a seat assembly may include a seat having a seat base and a seat back, an electronic control unit (ECU), a sensor assembly, and/or a response assembly. The ECU may be configured to determine via the sensor assembly whether an occupant disposed in the seat is in a first state, a second state, or a third state. The ECU may be configured to control the response assembly to change the state of said occupant from the first state to the second state and from the third state to the second state. The ECU may be configured to determine at least one of a breathing rate, a heart rate, and a heart rate variability of said occupant via the sensor assembly. The sensor assembly may include a biometric sensor and/or a piezoelectric sensor. The ECU may be configured to determine that said occupant is in the first state if (i) a heart rate of said occupant is below a heart rate threshold, (ii) a breathing rate of said occupant is below a breathing rate threshold, and/or (iii) a heart rate variability of said occupant is above a heart rate variability threshold.

With embodiments, an ECU may be configured to determine an occupant is in the second state if (i) a heart rate of said occupant is between a first heart rate threshold and a second heart rate threshold, (ii) a breathing rate of said occupant is between a first breathing rate threshold and a second breathing rate threshold, and/or (iii) a heart rate variability of said occupant is between a first heart rate variability threshold and a second heart rate variability threshold. The ECU may be configured to determine said occupant is in the third state if (i) a heart rate of said occupant is above a heart rate threshold, (ii) a breathing rate of said occupant is above a breathing rate threshold, and/or (iii) a heart rate variability of said occupant is below a heart rate variability threshold. The ECU may be configured to activate the response assembly according to the determined state of said occupant. If the ECU determines said occupant is in the first state, the ECU may be configured to activate the response assembly to increase a heart rate of said occupant, increase a breathing rate of said occupant, and/or decrease a heart rate variability of said occupant. The response assembly may include a haptic unit, a temperature control unit, a massage unit, a seat position unit, and/or an audio unit.

In embodiments, if the ECU determines said occupant is in the first state, the ECU may be configured to (i) vibrate the seat via a haptic unit of the response assembly at a high intensity, (ii) decrease a temperature proximate the seat via a temperature control unit of the response assembly, (iii) massage said occupant via a massage unit of the response assembly at a high intensity, (iv) increase a volume of sound proximate the seat via an audio unit of the response assembly, (v) place said occupant in a more upright position, and (vi) make at least one of the seat base and the seat back firmer via one or more bladders. If the ECU determines said occupant is in the third state, the ECU may be configured to activate the response assembly to decrease a heart rate of said occupant, decrease a breathing rate of said occupant, and/or increase a heart rate variability of said occupant. If the ECU determines said occupant is in the third state, the ECU may be configured to (i) vibrate the seat via a haptic unit of the response assembly at a low-intensity, (ii) massage said occupant via a massage unit of the response assembly at a low-intensity, and/or (iii) decrease a volume of sound proximate the seat via an audio unit of the response assembly.

With embodiments, an ECU may be configured to determine an effectiveness of an action of the response assembly according to a change in a heart rate, a breathing rate, and/or a heart rate variability of said occupant. The ECU may be configured to detect a specific occupant and create a profile of said occupant and store information from the sensor assembly to the profile. The profile may include information regarding the effectiveness of the action of the response assembly for changing the state of the specific occupant associated with the profile. The ECU may be configured to activate opposite response assembly actions when changing the state of said occupant from the first state to the second state relative to changing the state of said occupant from the third state to the second state. A seat assembly may include a fidget unit. The ECU may be configured to activate the fidget unit when said occupant is in the second state. The fidget unit may include at least one bladder and a fidget sensor. The bladder and the fidget sensor may be configured to detect whether said occupant is fidgeting.

In embodiments, a method of operating a seat assembly may include providing a seat; determining a heart rate, a breathing rate, and a heart rate variability of said occupant in the seat via a sensor assembly; determining whether said occupant is in a first state, a second state, or a third state via an electronic control unit; and/or changing the state of said occupant from the first state to the second state and from the third state to the second state via a response assembly. The first state may be a state of hypo-reactivity. The second state may be a state of normal activity. The third state may be a state of hyper-reactivity.

The foregoing and other aspects, features, details, utilities, and/or advantages of embodiments of the present disclosure

DETAILED DESCRIPTION

Reference will now be made in detail to embodiments of the present disclosure, examples of which are described herein and illustrated in the accompanying drawings. While the present disclosure will be described in conjunction with embodiments and/or examples, it will be understood that they do not limit the present disclosure to these embodiments and/or examples. On the contrary, the present disclosure covers alternatives, modifications, and equivalents.

Figure 1A:
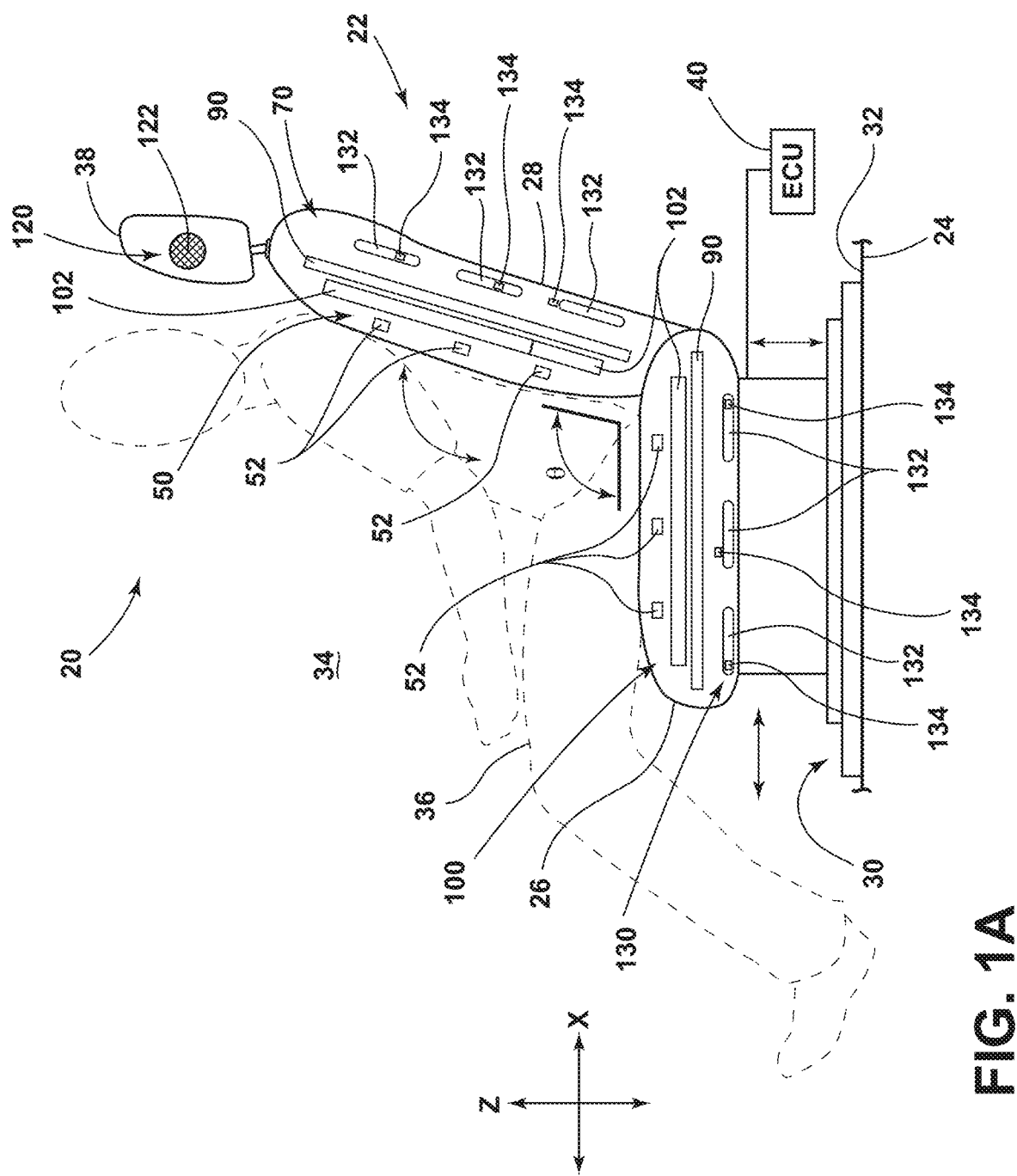
FIG. 1A is a side view of a portion of an embodiment of a seat assembly according to teachings of the present disclosure.
Figure 1B:
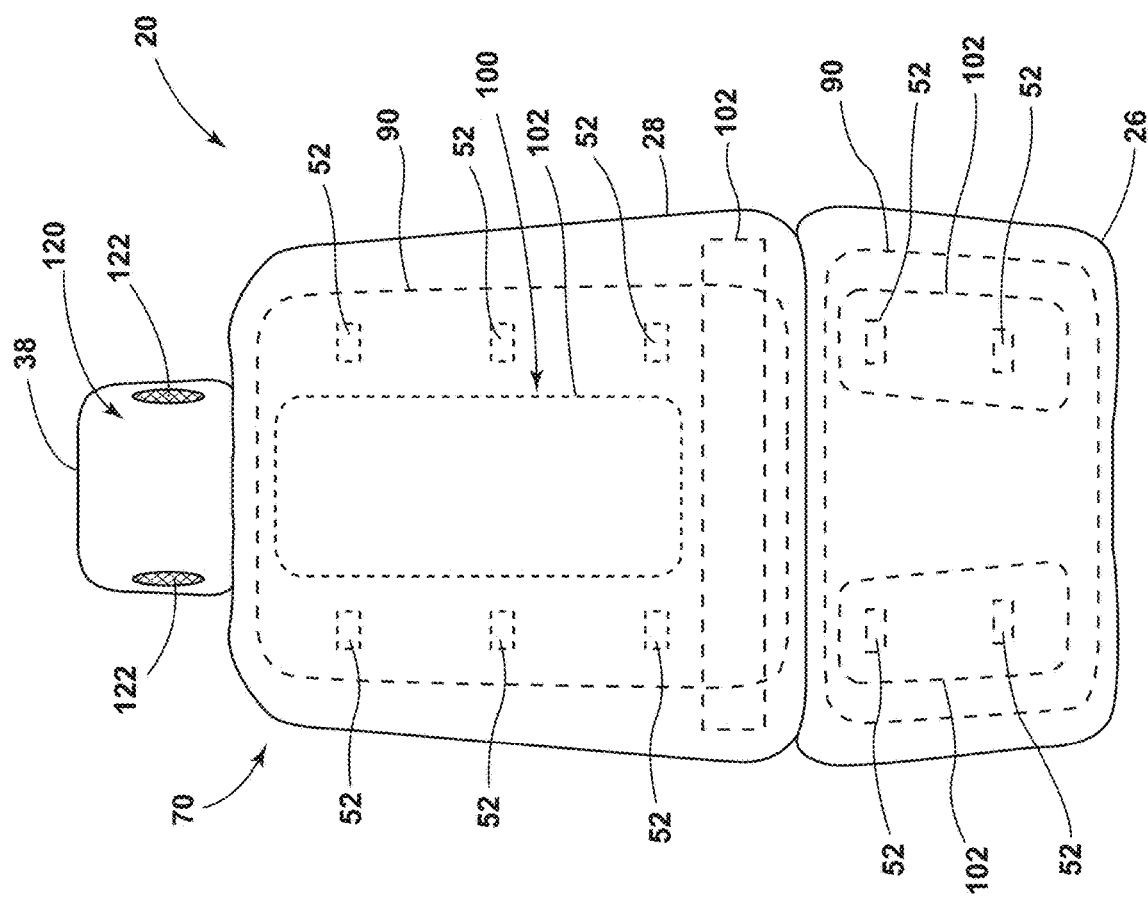
FIG. 1B is a front view of a portion of an embodiment of a seat assembly according to teachings of the present disclosure.
Figure 2:
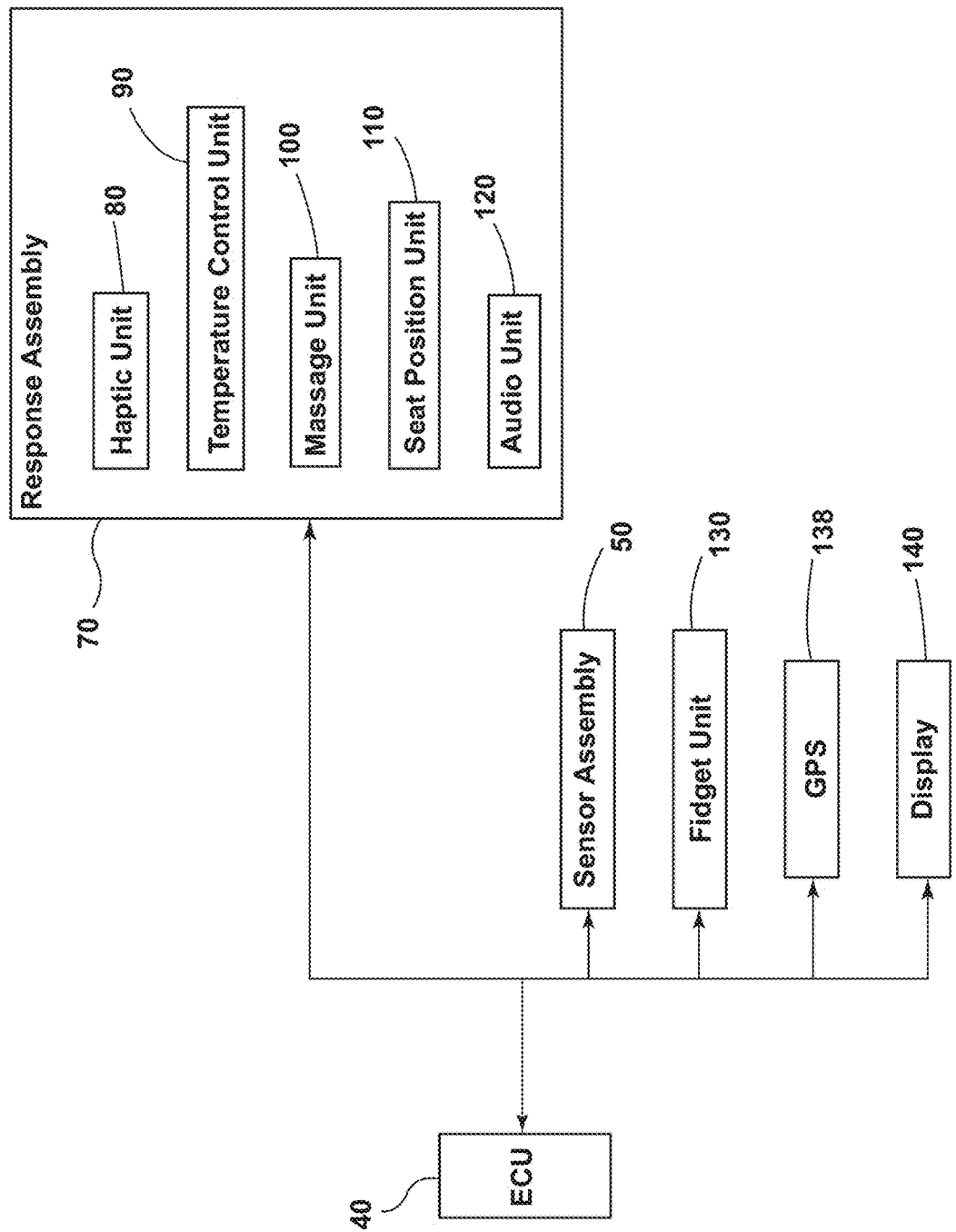
FIG. 2 is a schematic of a portion of an embodiment of a seat assembly according to teachings of the present disclosure.

In embodiments, such as generally illustrated in FIGS. 1A, 1B, and 2, a seat assembly 20 may include a seat 22, an electronic control unit (ECU) 40, a sensor assembly 50, and/or a response assembly 70. The seat assembly 20 may be configured to sense and/or change a state (e.g., a physical state) of an occupant 36 in the seat 22. The seat assembly 20 may be substantially disposed in a vehicle 24. The seat 22 may include a seat base 26 and/or a seat back 28. The seat 22 may be connected to a track assembly 30. The track assembly 30 may be connected to a mounting surface 32 (e.g., a floor of a vehicle 24). The seat 22 may be configured to move in an X-direction via the track assembly 30.

With embodiments, the ECU 40 may be connected (electrically and/or mechanically) to the seat 22 and/or may be disposed in the seat 22 and/or a vehicle cabin 34. The seat assembly 20 may include a sensor assembly 50 and/or a response assembly 70. The ECU 40 may be configured to communicate with and/or control the sensor assembly 50 and/or the response assembly 70. For example and without limitation, the ECU 40 may be configured to receive information from the sensor assembly 50 and the ECU 40 may be configured to send information to the response assembly 70 and/or receive information from the response assembly 70.

In embodiments, a seat assembly 20 may include a sensor assembly 50. The sensor assembly 50 may be configured to collect biometric information regarding an occupant 36 that may be seated in the seat 22. A non-limiting example of a sensor assembly is generally described in U.S. Pat. No. 10,034,631, which is hereby incorporated by reference as though fully set forth herein. A sensor assembly 50 may be configured to sense (e.g., measure, monitor, detect, obtain, determine, etc.) characteristics, such as biometric data, of an occupant 36 and/or may transmit the information to the ECU 40. The sensor assembly 50 may include one or more sensors 52 that may include a biometric sensor and/or a piezoelectric sensor. The sensors 52 may collect biometric information regarding the occupant 36 when the occupant 36 is in contact with and/or near the seat 22. The sensors 52 may be disposed in, disposed proximate, and/or connected to the seat base 26 and/or the seat back 28 of the seat 22. The sensor assembly 50 may be configured to sense vital information of an occupant 36 seated in the respective seat 22. For example and without limitation, the sensor assembly 50 may measure and/or collect data regarding the heart rate, the breathing rate, and/or the heart rate variability of an occupant 36. The sensor assembly 50 may be configured to transmit the vital information of the occupant 36 to the ECU 40 and the ECU 40 may determine a state of an occupant 36 according to (e.g., based on, utilizing, etc.), at least in part, the vital information.

With embodiments, the ECU 40 and/or the sensor assembly 50 may be configured to determine a state of an occupant 36. For example and without limitation, the ECU 40 may be configured to determine whether an occupant 36 is in a first state, a second state, and/or a third state. Determining the state of an occupant 36, may include the ECU 40 comparing information from the sensor assembly 50 to one or more of a variety of thresholds. For example and without limitation, the ECU 40 may compare information from the sensors 52 to a first breathing rate threshold, a second breathing rate threshold, a first heart rate threshold, a second heart rate threshold, a first heart rate variability threshold, and/or a second heart rate variability threshold. The first thresholds may include a value less than the second thresholds. For example, the first breathing rate threshold may be less than the second breathing rate threshold, the first heart rate threshold may be less than the second heart rate threshold, and/or the first heart rate variability threshold may be less than the second heart rate variability threshold.

In embodiments, the first state may correspond to an occupant 36 that may be in a state of hypo-reactivity and/or may not be sufficiently alert to operate a vehicle 24. In a state of hypo-reactivity, the vital information of the occupant 36 may not all be between the first thresholds and the second thresholds. For example and without limitation, when the occupant 36 is in the first state, the heart rate of the occupant 36 may be below (e.g., less than) the first heart rate threshold; the breathing rate of the occupant 36 may be below (e.g., less than) the first breathing rate threshold; and/or the heart rate variability of the occupant 36 may be above (e.g., greater than) the second heart rate variability threshold.

With embodiments, the second state may correspond to an occupant 36 that may not be in a state of hypo-reactivity or hyper-reactivity. For example, if an occupant 36 is in the second state, the occupant 36 may be in a normal or healthy condition (e.g., the occupant 36 may be sufficiently alert and/or responsive to operate a vehicle 24). The sensor assembly 50 may sense normal conditions for the vitals of an occupant 36 if the occupant 36 is in the second state. For example and without limitation, when the occupant 36 is in the second state, the heart rate of the occupant 36 may be between the first heart rate threshold and the second heart rate threshold; the breathing rate of the occupant 36 may be between the first breathing rate threshold and the second breathing rate threshold; and/or the heart rate variability of the occupant 36 may be between the first heart rate variability threshold and the second heart rate variability threshold.

In embodiments, the third state may correspond to an occupant 36 being in a state of hyper-reactivity, high stress, and/or agitation, which may not be ideal for operating a vehicle 24. In a state of hyper-reactivity, the vital information of the occupant 36 may not all be between the first thresholds and the second thresholds. For example and without limitation, when the occupant 36 is in the third state, the heart rate of the occupant 36 may be above (e.g., greater than) the second heart rate threshold; the breathing rate of the occupant 36 may be above (e.g., greater than) the second breathing rate threshold; and/or the heart rate variability of the occupant 36 may be below (e.g., less than) the first heart rate variability threshold.

With embodiments, such as generally illustrated in FIG. 2, the seat assembly 20 may include a response assembly 70. The ECU 40 may be configured to communicate with and/or control the response assembly 70. The ECU 40 may be configured to receive information from the sensor assembly 50 and/or activate the response assembly 70 according to the received information. The ECU 40 may be configured to compare information from the sensor assembly 50 to the thresholds to determine how to activate the response assembly 70 to change the state of the occupant 36 from the current state to the second state (if the occupant 36 is not already in the second state). The response assembly 70 may include one or more of a variety of units. For example and without limitation, the response assembly 70 may include a haptic unit 80, a temperature control unit 90, a massage unit 100, a seat position unit 110, and/or an audio unit 120, among others.

In embodiments, such as generally illustrated in FIG. 2, a response assembly 70 may include a haptic unit 80. The ECU 40 may be configured to control the haptic unit 80. The haptic unit 80 may be disposed in the seat base 26 and/or the seat back 28. The haptic unit 80 may be configured to send a vibration and/or an impulse to the occupant 36 through the seat base 26 and/or the seat back 28. A haptic unit 80 may, for example and without limitation, include one or more electric motors connected to unbalanced loads. The haptic unit 80 may be configured to send one or more of a variety of different impulses. For example and without limitation, the haptic unit 80 may transmit a quick impulse, a slow impulse, a strong impulse, and/or a weak impulse to the occupant 36.

With embodiments, such as generally illustrated in FIGS. 1A, 1B, and 2, a response assembly 70 may include a temperature control unit 90. The ECU 40 may be configured to control the temperature control unit 90. The temperature control unit 90 may or may not be connected to an HVAC module of a vehicle 24. The temperature control unit 90 may be configured to change the temperature (e.g., an air temperature and/or a surface temperature) of an area proximate the seat 22 and/or the occupant 36. The temperature control unit 90 may be configured to control the direction of air flow and/or the speed of air flow to the occupant 36. The temperature control unit 90 may be connected to the seat base 26 and/or seat back 28, such as to provide heated seat and/or ventilated seat functions. The temperature control unit 90 may be configured to increase and/or decrease the air temperature of the vehicle cabin 34, the temperature of the seat base 26, and/or the temperature of the seat back 28.

In embodiments, such as generally illustrated in FIGS. 1A, 1B, and 2, a response assembly 70 may include a massage unit 100, and/or the ECU 40 may be configured to control the massage unit 100. The massage unit 100 may include one or more massagers 102 that may be configured to massage an occupant 36. The seat base 26 and/or the seat back 28 may include one or more massagers 102. The massagers 102 may be configured to inflate, deflate, and/or actuate. The massagers 102 may be configured to operate at a high speed, low speed, high intensity, and/or low intensity. The massage unit 100 may be configured to operate in a first mode and/or a second mode. In the first mode, at least one massager 102 may be operated at a high speed and/or high intensity. In the second mode, at least one massager 102 may be operated at a low speed and/or low intensity. In embodiments, the haptic unit 80 and the massage unit 100 may, for example and without limitation, be integrated with each other and/or may be the same unit.

With embodiments, such as generally illustrated in FIG. 2, a response assembly 70 may include a seat position unit 110. The ECU 40 may be configured to control the seat position unit 110. The seat position unit 110 may be configured to move the seat 22 in the X-direction, Y-direction, and/or Z-direction, rotate the seat 22, tilt the seat 22, and/or move the seat 22. For example and without limitation, the seat position unit 110 may include one or more motors that may be connected to the seat base 26, the seat back 28, and/or the track assembly 30. The seat position unit 110 may change the angle of the seat base 26 and/or the seat back 28. The seat position unit 110 may increase and/or decrease the angle $\theta$ between the seat base 26 and the seat back 28. The seat position unit 110 may change the position of the seat 22 between a relaxed position and an upright position. The relaxed position may include an angle $\theta$ between the seat base 26 and the seat back 28 that may be greater than the angle $\theta$ of the seat base 26 and the seat back 28 when in the upright position.

With embodiments, such as generally illustrated in FIGS. 1A, 1B, and 2, the response assembly 70 may include an audio unit 120. The ECU 40 may be configured to control the audio unit 120. The audio unit 120 may be connected to a sound system of a vehicle 24. The audio unit 120 may include one or more speakers 122 that may be disposed in the vehicle cabin 34. For example and without limitation, one or more speakers 122 may be disposed on the seat base 26 and/or the seat back 28. One or more speakers 122 may be disposed on/in the seat back 28, such as proximate a head of an occupant 36 (e.g., the speakers 122 may be disposed near the headrest 38). The audio unit 120 may be configured to control the volume and/or the content of sound played within the vehicle cabin 34. For example and without limitation, the audio unit 120 may be configured to play soothing music and/or vigorous music. The audio unit 120 may be configured to increase and/or decrease the volume of the sound in the vehicle cabin 34. The audio unit 120 may be configured to broadcast an audio alert to an occupant 36. The alert may include an inquiry to the occupant 36 about whether the occupant 36 desires to take a break from operating the vehicle 24. If the occupant 36 responds in the positive, the ECU 40 may activate a global positioning system (GPS) unit 138 to determine the closest location to safely stop the vehicle 24, such as rest area or point of interest (e.g., restaurant, coffee shop, gas station, etc.). If the occupant 36 responds in the negative, the ECU 40 may inquire again after an amount of time.

With embodiments, the ECU 40 may be configured to activate at least one of the haptic unit 80, the temperature control unit 90, the massage unit 100, the seat position unit 110, and/or the audio unit 120 in accordance with the determined state of the occupant 36. The ECU 40 may be configured to activate units of the response assembly 70 in different manners based on whether the occupant 36 is in the first state, the second state, and/or the third state.

In embodiments, if the ECU 40 determines that the occupant 36 is in the first state, such as via the sensor assembly 50, the ECU 40 may activate the response assembly 70 to change the state of the occupant 36 from the first state to the second state. For example and without limitation, the ECU 40 may be configured to activate the response assembly 70 to increase the heart rate of the occupant 36, increase the breathing rate of the occupant 36, and/or decrease the heart rate variability of the occupant 36. If the occupant 36 is in the first state, the ECU 40 may be configured to activate the haptic unit 80, the temperature control unit 90, the massage unit 100, the seat position unit 110, and/or the audio unit 120. The ECU 40 may measure and/or store the information of the occupant 36 regarding the heart rate, the breathing rate, and/or the heart rate variability prior to activating the response assembly 70. The ECU 40 may be configured to increase the heart rate of the occupant 36 until the heart rate is between a first heart rate threshold and a second heart rate threshold (e.g., between a lower nominal value and an upper nominal value). The ECU 40 may be configured to increase the breathing rate of the occupant 36 until the breathing rate is between the first breathing rate threshold and the second breathing rate threshold. The ECU 40 may be configured to decrease the heart rate variability of the occupant 36 until the heart rate variability is between the first heart rate variability threshold and the second heart rate variability threshold. The ECU 40 may measure and/or store the information of the occupant 36 regarding the heart rate, the breathing rate, and/or the heart rate variability after activating the response assembly 70.

With embodiments, activating the response assembly 70 to change the state of the occupant 36 from the first state to the second state may include the ECU 40 activating the haptic unit 80 to transmit a strong/quick impulse to the occupant 36 via the seat base 26 and/or the seat back 28. Additionally or alternatively, the ECU 40 may activate the temperature control unit 90 to change the state of the occupant 36 from the first state to the second state. For example and without limitation, the ECU 40 (via the temperature control unit 90) may decrease the temperature inside the vehicle cabin 34, direct air flow in a direction towards the occupant 36, increase the speed of air flow, and/or activate the seat base 26 and/or seat back 28 ventilation functions, one or more of which may generally lead to an increase in heart rate, an increase in breathing rate, and/or a decrease in heart rate variability. The ECU 40 may activate the massage unit 100 to change the state of the occupant 36 from the first state to the second state. For example and without limitation, the ECU 40 (via the massage unit 100) may activate one or more massagers 102 in the seat base 26 and/or the seat back 28 in a first mode (e.g., high speed/high intensity). The ECU 40 may activate the seat position unit 110 to change the state of the occupant 36 from the first state to the second state. For example and without limitation, the ECU 40 (via the seat position unit 110) may decrease the angle θ between the seat base 26 and the seat back 28, which may result in the seat 22 being disposed in a more upright position, which may tend to make the occupant 36 more alert. The ECU 40 may activate the audio unit 120 to change the state of the occupant 36 from the first state to the second state. For example and without limitation, the ECU 40 (via the audio unit 120) may increase the volume of sound (e.g., music) inside the vehicle cabin 34 and/or the audio unit 120 may play vigorous sounds/music. Additionally or alternatively, the ECU 40 may activate an audio alert to indicate to the occupant 36 that a rest area (e.g., rest stop, restaurant, gas station, etc.) is nearby.

In embodiments, if the ECU 40 determines that the occupant 36 is in the third state, such as via the sensor assembly 50, the ECU 40 may activate the response assembly 70 to change the state of the occupant 36 from the third state to the second state. For example and without limitation, the ECU 40 may be configured to activate the response assembly 70 to decrease the heart rate of the occupant 36, decrease the breathing rate of the occupant 36, and/or increase the heart rate variability of the occupant 36. If the occupant 36 is in the third state, the ECU 40 may, for example, be configured to activate the haptic unit 80, the massage unit 100, the seat position unit 110, and/or the audio unit 120. The ECU 40 may measure and/or store the information of the occupant 36 regarding the heart rate, the breathing rate, and/or the heart rate variability prior to activating the response assembly 70. The ECU 40 may be configured to decrease the heart rate of the occupant 36 until the heart rate is between the first heart rate threshold and the second heart rate threshold. The ECU 40 may be configured to decrease the breathing rate of the occupant 36 until the breathing rate is between the first breathing rate threshold and the second breathing rate threshold. The ECU 40 may be configured to increase the heart rate variability of the occupant 36 until the heart rate variability is between the first heart rate variability threshold and the second heart rate variability threshold. The ECU 40 may measure and/or store the information of the occupant 36 regarding the heart rate, the breathing rate, and/or the heart rate variability after activating the response assembly 70 (e.g., may store an effectiveness of various activations of the response assembly 70 for the particular occupant 36).

With embodiments, changing the state of the occupant 36 from the third state to the second state may, for example, include the ECU 40 activating the haptic unit 80 to transmit a weak/slow impulse to the occupant 36 via the seat base 26 and/or the seat back 28. Additionally or alternatively, the ECU 40 may activate the massage unit 100 to change the state of the occupant 36 from the third state to the second state. For example and without limitation, the ECU 40 (via the massage unit 100) may activate one or more massagers 102 in the seat base 26 and/or the seat back 28 in a second mode (e.g., low speed/low intensity). The ECU 40 may activate the seat position unit 110 to change the state of the occupant 36 from the third state to the second state. For example and without limitation, the ECU 40 (via the seat position unit 110) may increase the angle θ between the seat base 26 and the seat back 28, such as to provide a more reclined or relaxed seating configuration. The ECU 40 may activate the audio unit 120 to change the state of the occupant 36 from the third state to the second state. For example and without limitation, the ECU 40 (via the audio unit 120) may decrease the volume of sound (e.g., music) inside the vehicle cabin 34 and/or the audio unit 120 may play soothing sounds/music. Additionally or alternatively, the ECU 40 may alert and/or inform the occupant 36 that the occupant 36 may need a break from operating the vehicle 24 (if seated in the driver seat) and/or may activate an audio alert to indicate to the occupant 36 that a rest area (e.g., rest stop, restaurant, gas station, etc.) is nearby.

With embodiments, if the ECU 40 determines that the occupant 36 is in the second state, such as via the sensor assembly 50, the ECU 40 may not activate the response assembly 70 to change the heart rate, the breathing rate, and/or the heart rate variability of the occupant 36. When the occupant 36 is in the second state, the sensor assembly 50 may continue to sense the heart rate, the breathing rate, and/or the heart variability in order to detect if the state of the occupant 36 changes from the second state to the first state and/or the third state.

In embodiments, such as generally illustrated in FIGS. 1A, 1B, and 2, the seat assembly 20 may include a fidget unit 130, and/or the fidget unit 130 may be connected to the ECU 40. The ECU 40 may be configured to control the fidget unit 130. The fidget unit 130 may be configured to determine whether an occupant 36 is fidgeting, which may suggest that the occupant 36 is not comfortable. The fidget unit 130 may be activated, for example, when the occupant 36 in in the second state. The fidget unit 130 may include one or more actuators (e.g., bladders) 132 that may be configured to inflate and/or deflate. The ECU 40 may be configured to control the inflation and/or deflation of the bladders 132. The bladders 132 may be at least partially disposed in the seat base 26 and/or the seat back 28. The bladders 132 may include and/or be connected to one or more sensors 134 that may be configured to sense changes in pressure in the bladders 132, which may correspond to movement (e.g., fidgeting) of the occupant 36. The ECU 40 may be configured to inflate and/or deflate the bladders 132 to reduce the severity and/or amount of fidgeting (e.g., to make the occupant 36 more comfortable). The fidget unit 130 may be connected to and/or include one or more units of the response assembly 70, such as, for example and without limitation, the massage unit 100.

In embodiments, the ECU 40 may be configured to detect an occupant 36, retrieve a profile of an occupant 36, and/or store/modify a profile of an occupant 36. The ECU 40 may be connected to one or more biometric sensors 52 of the sensor assembly 50 that may be configured to detect/identify a specific occupant 36 that may be seated in a seat 22. If the ECU 40 is unable to identify an occupant 36, the ECU 40 may create a new profile for the occupant 36. The profile of the occupant 36 may include information including the effectiveness of actions (of units) of the response assembly 70. For example and without limitation, the ECU 40 may be configured to measure the effectiveness of a specific unit of the response assembly 70 on the heart rate, the breathing rate, and/or the heart rate variability of the occupant 36.

With embodiments, the ECU 40 may obtain the heart rate, the breathing rate, and/or the heart rate variability of the occupant 36 prior to activating a unit of the response assembly 70; and/or the ECU 40 may obtain the heart rate, the breathing rate, and/or the heart rate variability of the occupant 36 after activating a unit of the response assembly 70. The ECU 40 may record the amount the response assembly 70 affected the heart rate, the breathing rate, and/or the heart rate variability of the occupant 36. The stored profile of an occupant 36 may include information regarding the more effective units of the response assembly 70, and/or the ECU 40 may prioritize adjusting the more effective units when changing the state of the occupant 36 from the first state or third state to the second state. The ECU 40 may store one or more occupant profiles, and/or each profile may prioritize different units when changing the heart rate, the breathing rate, and/or the heart rate variability of the occupant 36.

In embodiments, the ECU 40 may be configured to analyze an occupant profile, and/or the ECU 40 may be configured to determine a response (e.g., an activation of the response assembly 70) that may be effective in changing the state of the occupant 36 from the third state to the second state based on information relating to previously changing the state of the occupant 36 from the first state to the second state. The ECU 40 may analyze the effective units of the response assembly 70 in increasing the heart rate, increasing the breathing rate, and/or decreasing the heart rate variability of the occupant 36; and/or the ECU 40 may activate the units in an opposite/inverse manner to decrease the heart rate, decrease the breathing rate, and/or increase the heart rate variability of the occupant 36. For example and without limitation, if the occupant profile includes information indicating that activating the massage unit 100 to massage the occupant 36 in the first mode (e.g., high intensity/high frequency) increased the heart rate and/or the breathing rate of the occupant 36, the ECU 40 may activate the massage unit 100 to massage the occupant 36 in the second mode (e.g., low intensity/low frequency) to decrease the heart rate and/or the breathing rate of the occupant 36. The ECU 40 may monitor the effectiveness of the response on the heart rate, the breathing rate, and/or the heart rate variability of the occupant 36, and/or the ECU 40 may store the response information with the occupant profile.

Figure 3:
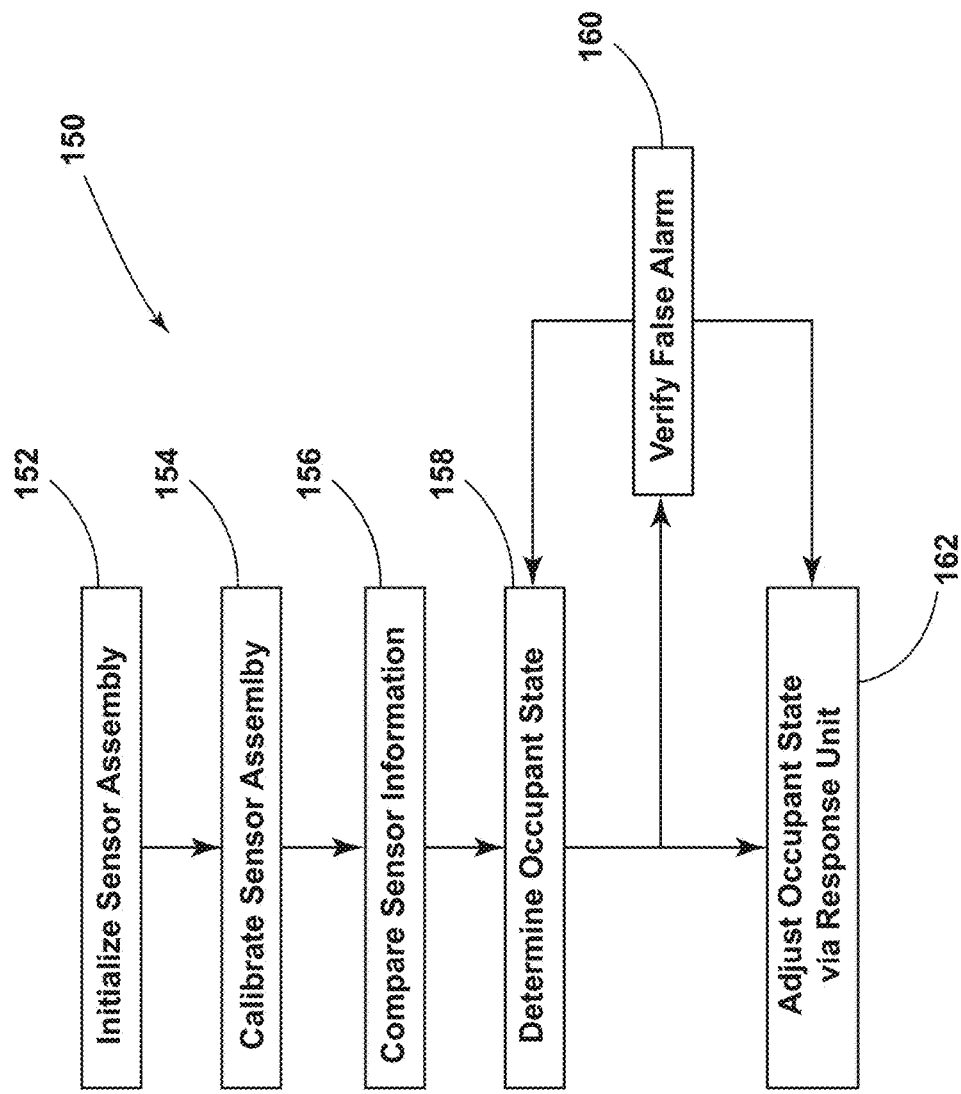
FIG. 3 is a flow chart generally illustrating an embodiment of a method of operating seat assembly according to teachings of the present disclosure.

With embodiments, such as generally illustrated in FIG. 3, a method 150 of operating a seat assembly 20 may include providing a seat 22, an ECU 40, a sensor assembly 50, and/or a response assembly 70. The method 150 may include initializing the sensor assembly 50 (step 152). Initializing the sensor assembly 50 may include determining whether an occupant 36 is seated in the seat 22, providing power to the sensor assembly 50, determining whether the ECU 40 includes an associated occupant profile, and/or creating a profile for an unidentified occupant 36. If a profile of an occupant 36 is not identified, the ECU 40 may create a profile including and/or associated with biometric data of the occupant 36 that may be obtained via one or more biometric sensors. The method 150 may include calibrating the sensor assembly 50 (step 154). Calibrating the sensor assembly 50 may include a delay (e.g., about 10-15 seconds or more or less) to measure biometric information of the occupant 36 over a period of time. The ECU 40 may display a message to a display 140 that may indicate to an occupant 36 to sit still (e.g., to receive accurate measurements/data). The ECU 40 may activate the sensors 52 of the sensor assembly 50 to test the functionality. If the sensors 52 successfully gather information of the occupant 36, sensor calibration (step 154) may be completed. If the sensors 52 do not gather information of the occupant 36 (e.g., the data is corrupt, a sensor malfunctions, etc.), the ECU 40 may restart the sensor calibration (step 154).

In embodiments, a method 150 of operating a seat assembly 20 may include comparing information from the sensor assembly 50 to one or more thresholds (step 156). Comparing the sensor assembly data (step 156) may include comparing the sensed heart rate, the breathing rate, and/or the heart variability to an average heart rate, an average breathing rate, and/or an average heart rate variability associated with an occupant profile. If the sensed values of the heart rate, the breathing rate, and/or the heart rate variability are not substantially similar to the stored averages (e.g., within threshold values or ranges), the ECU 40 may transmit a notification to the display 140, such as a suggestion that the occupant 36 should contact a medical professional.

Figure 4:
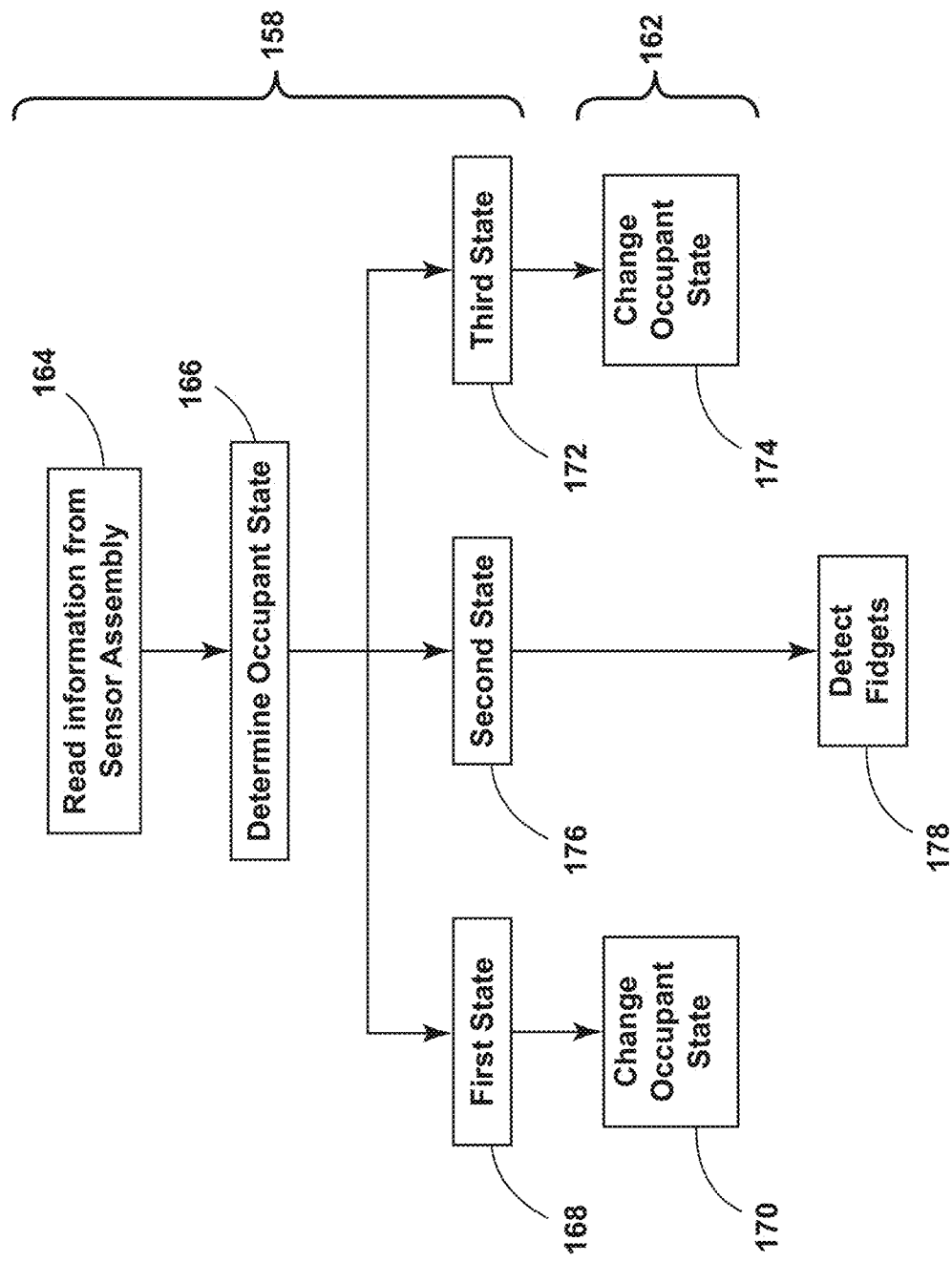
FIG. 4 is a flow chart generally illustrating an embodiment of a method of determining and changing the state of an occupant according to teachings of the present disclosure.

With embodiments, such as generally illustrated in FIGS. 3 and 4, a method 150 of operating a seat assembly 20 may include determining the state of the occupant 36 (step 158). In determining the state of the occupant 36, the ECU 40 may receive information from the sensor assembly 50. The ECU 40 may activate the sensor assembly 50 to sense the heart rate, the breathing rate, and/or the heart rate variability of the occupant 36. The ECU 40 may compare the heart rate, the breathing rate, and/or the heart rate variability of the occupant 36 to the respective first thresholds and the second thresholds of the heart rate, the breathing rate, and/or the heart rate variability. The method 150 of operating the seat assembly 20 may include verifying a false alarm (step 160). If the measured heart rate, the breathing rate, and/or the heart rate variability is not measured correctly and/or is not between the thresholds, the ECU 40 may transmit an alert to the display 140 inquiring whether the occupant 36 would like to stop the vehicle 24 to re-measure via the sensor assembly 50. If the occupant 36 responds in the affirmative, the ECU 40 may wait until the vehicle 24 is in park/stopped to restart one or more steps of the method 150, such as activating the sensor assembly 50 (step 152) and/or remeasuring the heart rate, the breathing rate, and/or the heart rate variability (step 158). If the remeasured heart rate, breathing rate, and/or heart rate variability is outside the thresholds, the ECU 40 may be configured to transmit a warning to a vehicle assistance program (e.g., that may be connected to a wireless network, such as, for example and without limitation, a cellular connection to OnStar). If the ECU 40 receives correct data from the sensor assembly 50, the ECU 40 may adjust the state of the occupant 36 (step 162).

In embodiments, such as generally illustrated in FIGS. 3 and 4, a method 150 of operating the seat assembly 20 may include determining the state of the occupant 36 (step 158) and/or changing the state of the occupant 36 (step 162). The ECU 40 may read/receive information from the sensor assembly (step 164), and/or determine the state of the occupant 36 (step 166). If the occupant 36 is determined by the ECU 40 to be in the first state (step 168), the ECU 40 may be configured to activate the haptic unit 80, the temperature control unit 90, the massage unit 100, the seat position unit 110, and/or the audio unit 120 to change the state of the occupant 36 from the first state to the second state (step 170). If the occupant 36 is determined by the ECU 40 to be in the third state (step 172), the ECU 40 may be configured to activate the haptic unit 80, the massage unit 100, the seat position unit 110, and/or the audio unit 120 to change the state of the occupant 36 from the third state to the second state (step 174).

With embodiments, such as generally illustrated in FIG. 4, a method 150 of operating a seat assembly 20 may include detecting fidgets (e.g., detecting movement of the occupant 36 in the seat 22) (step 178). If the ECU 40 determines that the occupant 36 is in the second state (step 176), the ECU 40 may detect fidgets of the occupant 36 (step 178). If the ECU 40 determines that the occupant 36 is in the first state or the third state, the ECU 40 may not activate the fidget unit 130 and/or may not detect fidgets. The ECU 40 may prioritize changing the state of the occupant 36 from the first state and/or the third state to the second state over reducing the number and/or severity of fidgets.

Figure 5:
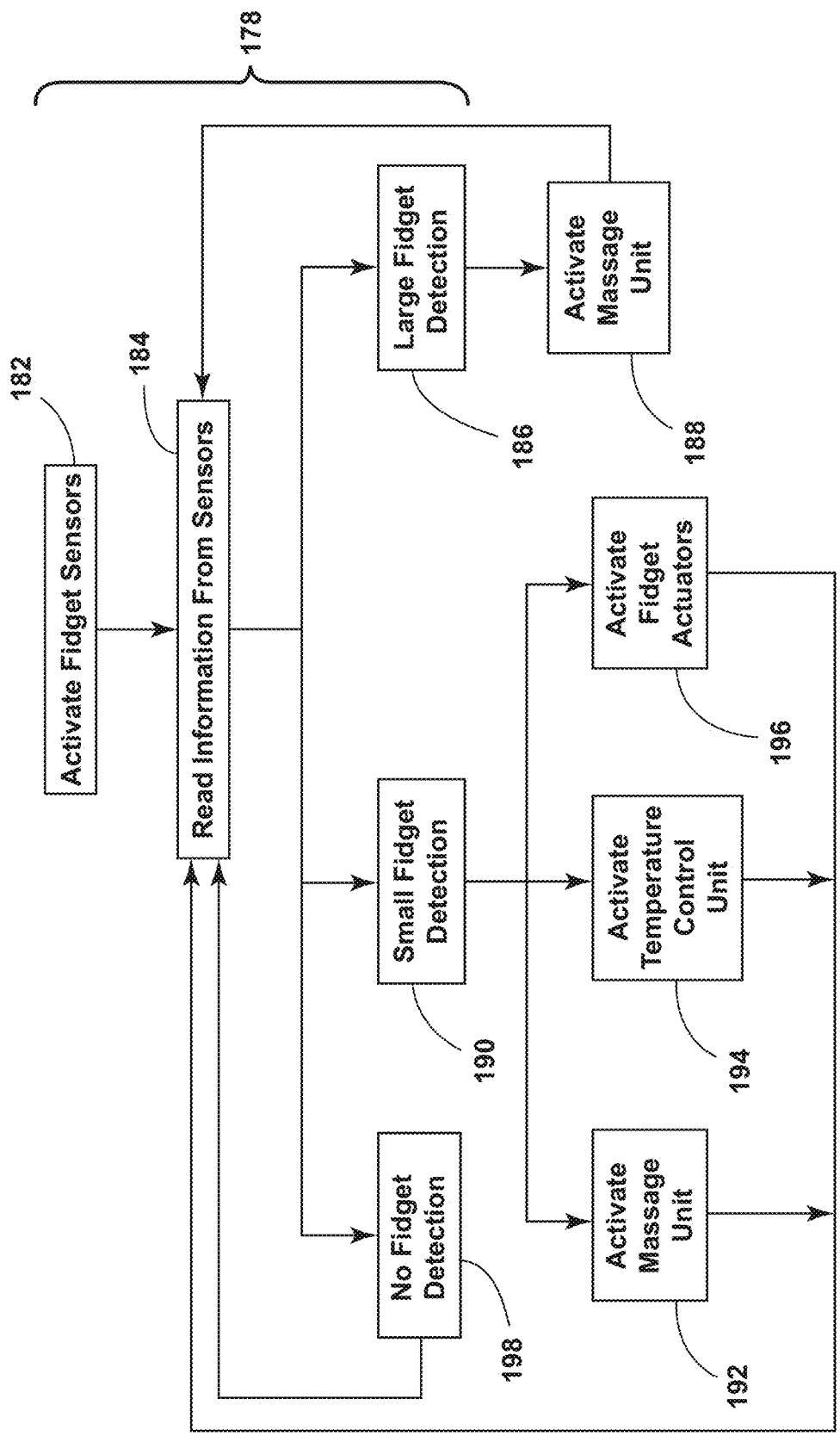
FIG. 5 is a flow chart generally illustrating an embodiment of a method of operating the fidget unit and portions of the response assembly according to teachings of the present disclosure.

In embodiments, such as generally illustrated in FIG. 5, detecting fidgets (step 178) may include activating the fidget sensors 134 (step 182), the ECU 40 receiving information from the fidget sensors 134 (step 184), and/or activating one or more units of the response assembly 70 (steps 188, 192, 194, 196) and/or the actuators 132 of the fidget unit 130. Receiving information from the fidget sensors 134 (step 184) may include measuring the number of fidgets of the occupant 36 (e.g., the number of movements of the occupant 36 in the seat 22 via the fidget sensors 134). The ECU 40 may analyze the fidget information to detect a large fidget (step 186) or detect a small fidget (step 190). If the ECU 40 detects a large fidget/significant fidgeting (step 186), the ECU 40 may activate the massage unit 100 (step 188). Activating the massage unit 100 may, for example, include massaging and/or stretching the spine of the occupant 36 via the massagers 102 of the massage unit 100 (e.g., the massagers 102 proximate the lumbar of the occupant 36 may be activated by the ECU 40). The ECU 40 may activate massagers 102 in the seat base 26 and/or the seat back 28 that may be proximate the location of the detected fidgets (e.g., as sensed via the fidget sensors 134). If the ECU 40 detects a small fidget/minor fidgeting (step 190), the ECU 40 may activate the massage unit 100 (step 192), the temperature control unit 90 (step 194), and/or activate the actuators 132 of the fidget unit 130 (e.g., inflate/deflate bladders) (step 196). For example and without limitation, the ECU 40 may activate massagers 102 proximate the lumbar of the occupant 36, the ECU 40 may reduce the temperature of the vehicle cabin 34 proximate the occupant 36, the ECU 40 may direct air flow in a direction towards the occupant 36, the ECU 40 may activate the ventilation function of the seat 22, and/or the ECU 40 may inflate/deflate bladders 132 proximate the sensed fidgets. If the number of measured fidgets is less than the second fidget threshold, the ECU 40 may detect insignificant or no fidgeting (step 198). If the ECU 40 detects insignificant fidgeting, the ECU 40 may continue to receive information from the fidget sensors 134 until the number of fidgets measured is greater than the second fidget threshold (e.g., the second fidget threshold may be less than the first fidget threshold).

In embodiments, the ECU 40 may be configured to operate the fidget unit 130 while determining/changing the state of an occupant 36, such as regardless of what state the occupant 36 is in. The ECU 40 may activate the response assembly 70 and the fidget unit 130 simultaneously to change the state of the occupant 36 and to reduce fidgeting. The ECU 40 may monitor patterns of the types of fidgeting of an occupant 36 when the occupant 36 is in each state, store such patterns in an occupant profile, and/or use such patterns in determining the state of the occupant 36. If there is a conflict between the actions for changing the state of the occupant 36 and reducing fidgeting, the actions for changing the state of the occupant 36 may supersede the actions for reducing fidgeting (e.g., changing the state of the occupant 36 may improve the safety of the occupant 36 and reducing fidgeting may improve the comfort of the occupant 36).

With embodiments, an ECU 40 may be configured to determine if an occupant 36 is a driver/operator or a passenger. If the occupant 36 is a passenger, the ECU 40 may activate the fidget unit 130 even if the ECU 40 determines that the occupant 36 is in the first state or the second state. For example and without limitation, a passenger may be in the first state if the passenger is attempting to sleep and the ECU 40 may activate the fidget unit 130 to make the passenger more comfortable (to facilitate sleep). If the occupant 36 is a passenger, the ECU 40 may not change the state of the occupant 36 from the first state to the second state unless requested by the occupant 36.

In embodiments, an ECU 40 may be configured to monitor an occupant 36 over a relatively long period of time (e.g., days, weeks, months, years, etc.) and/or across a plurality of instances of the occupant 36 sitting in a seat. For example and without limitation, the ECU 40 may determine, such as via the sensor assembly 50, that the heart rate of an occupant 36 is significantly higher than previously sensed (e.g., a week ago). The ECU 40 may be configured to alert an occupant 36 of changes and/or suggest that the occupant 36 seek medical assistance.

In embodiments, an ECU (e.g., ECU 40) may include an electronic controller and/or include an electronic processor, such as a programmable microprocessor and/or microcontroller. In embodiments, an ECU may include, for example, an application specific integrated circuit (ASIC). An ECU may include a central processing unit (CPU), a memory unit (e.g., a non-transitory computer-readable storage medium), and/or an input/output (I/O) interface. An ECU may be configured to perform various functions, including those described in greater detail herein, with appropriate programming instructions and/or code embodied in software, hardware, and/or other medium. In embodiments, an ECU may include a plurality of controllers. In embodiments, an ECU may be connected to a display (e.g., display 140), such as a touchscreen display.

Various embodiments are described herein for various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments.

Reference throughout the specification to "various embodiments," "with embodiments," "in embodiments," or "an embodiment," or the like, means that a particular feature, structure, or characteristic described in connection with the embodiment is included in at least one embodiment. Thus, appearances of the phrases "in various embodiments," "with embodiments," "in embodiments," or "an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment/example may be combined, in whole or in part, with the features, structures, functions, and/or characteristics of one or more other embodiments/examples without limitation given that such combination is not illogical or non-functional. Moreover, many modifications may be made to adapt a particular situation or material to the teachings of the present disclosure without departing from the scope thereof.

It should be understood that references to a single element are not necessarily so limited and may include one or more of such element. Any directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of embodiments.

Joinder references (e.g., attached, coupled, connected, and the like) are to be construed broadly and may include intermediate members between a connection of elements and relative movement between elements. As such, joinder references do not necessarily imply that two elements are directly connected/coupled and in fixed relation to each other. The use of "e.g." in the specification is to be construed broadly and is used to provide non-limiting examples of embodiments of the disclosure, and the disclosure is not limited to such examples. Uses of "and" and "or" are to be construed broadly (e.g., to be treated as "and/or"). For example and without limitation, uses of "and" do not necessarily require all elements or features listed, and uses of "or" are intended to be inclusive unless such a construction would be illogical.

While processes, systems, and methods may be described herein in connection with one or more steps in a particular sequence, it should be understood that such methods may be practiced with the steps in a different order, with certain steps performed simultaneously, with additional steps, and/or with certain described steps omitted.

It is intended that all matter contained in the above description or shown in the accompanying drawings shall be interpreted as illustrative only and not limiting. Changes in detail or structure may be made without departing from the present disclosure.

What is claimed is:

1. A seat assembly, comprising:
   a seat having a seat base and a seat back;
   an electronic control unit (ECU);
   a sensor assembly;
   a response assembly including at least one of a haptic unit, a temperature control unit, a massage unit, a seat position unit, and/or an audio unit; and
   a fidget unit including a fidget sensor;
   wherein the ECU is configured to determine via the sensor assembly whether an occupant disposed in the seat is in a first state, a second state, or a third state;
   the ECU is configured to control the response assembly to change the state of said occupant from the first state to the second state and from the third state to the second state; and
   the ECU is configured to operate the fidget unit while determining and changing the state of said occupant.

2. The seat assembly of claim 1, wherein the ECU is configured to determine at least one of a breathing rate, a heart rate, and a heart rate variability of said occupant via the sensor assembly.

3. The seat assembly of claim 1, wherein the response assembly includes the audio unit;
   the audio unit is configured to provide an inquiry to said occupant; and
   the ECU is configured to determine a stopping location according to information from said occupant regarding the inquiry.

4. The seat assembly of claim 1, wherein the ECU is configured to determine said occupant is in the second state if (i) a heart rate of said occupant is between a first heart rate threshold and a second heart rate threshold, (ii) a breathing rate of said occupant is between a first breathing rate threshold and a second breathing rate threshold, and (iii) a heart rate variability of said occupant is between a first heart rate variability threshold and a second heart rate variability threshold.

5. The seat assembly of claim 1, wherein the ECU is configured to determine said occupant is in the third state if (i) a heart rate of said occupant is above a heart rate threshold, (ii) a breathing rate of said occupant is above a breathing rate threshold, and (iii) a heart rate variability of said occupant is below a heart rate variability threshold.

6. The seat assembly of claim 1, wherein the ECU is configured to activate the response assembly according to the state of said occupant and whether said occupant is a driver or a passenger.

7. The seat assembly of claim 1, wherein if the ECU determines said occupant is in the first state, the ECU is configured to activate the response assembly to increase a heart rate of said occupant, increase a breathing rate of said occupant, and decrease a heart rate variability of said occupant.

8. The seat assembly of claim 1, wherein the response assembly includes the haptic unit, the temperature control unit, the massage unit, the seat position unit, and/or the audio unit.

9. The seat assembly of claim 1, wherein if the ECU determines said occupant is in the first state, the ECU is configured to (i) vibrate the seat via the haptic unit of the response assembly at a high intensity, (ii) decrease a temperature proximate the seat via the temperature control unit of the response assembly, (iii) increase a volume of sound proximate the seat via the audio unit of the response assembly, (iv) place said occupant in a more upright position via the seat position unit, and/or (v) make at least one of the seat base and the seat back firmer via one or more bladders.

10. The seat assembly of claim 1, wherein if the ECU determines said occupant is in the third state, the ECU is configured to activate the response assembly to decrease a heart rate of said occupant, decrease a breathing rate of said occupant, and/or increase a heart rate variability of said occupant.

11. The seat assembly of claim 1, wherein if the ECU determines said occupant is in the third state, the ECU is configured to (i) vibrate the seat via the haptic unit of the response assembly at a low-intensity, and/or (ii) decrease a volume of sound proximate the seat via the audio unit of the response assembly.

12. The seat assembly of claim 1, wherein the ECU is configured to determine an effectiveness of an action of the response assembly according to a change in a heart rate, a breathing rate, and/or a heart rate variability of said occupant.

13. The seat assembly of claim 1, wherein the ECU is configured to identify said occupant, create a profile of said occupant, and store information from the sensor assembly to the profile.

14. The seat assembly of claim 1, wherein the ECU is configured to prioritize actions for the response assembly over the fidget unit if there is a conflict between actions for changing the state of said occupant and reducing fidgeting.

15. The seat assembly of claim 1, wherein the fidget unit includes at least one bladder; and the ECU is configured to detect whether said occupant is fidgeting via the fidget sensor and/or the bladder.

16. The seat assembly of claim 1, wherein the ECU is configured to activate the fidget unit according to whether said occupant is a driver or a passenger.

17. The seat assembly of claim 1, wherein the ECU is configured not to operate the response assembly to change said occupant from the first state to the second state if said occupant is a passenger, unless requested by said occupant.

18. A seat assembly, comprising:
a seat having a seat base and a seat back;
an electronic control unit (ECU);
a sensor assembly; and
a response assembly;
wherein the ECU is configured to determine via the sensor assembly whether an occupant disposed in the seat is in a first state, a second state, or a third state;
the ECU is configured to control the response assembly to change the state of said occupant from the first state to the second state and from the third state to the second state; and
the ECU is configured to determine that said occupant is in the first state if (i) a heart rate of said occupant is below a heart rate threshold, (ii) a breathing rate of said occupant is below a breathing rate threshold, and (iii) a heart rate variability of said occupant is above a heart rate variability threshold.

19. A seat assembly, comprising:
a seat having a seat base and a seat back;
an electronic control unit (ECU);
a sensor assembly; and
a response assembly;
wherein the ECU is configured to determine via the sensor assembly whether an occupant disposed in the seat is in a first state, a second state, or a third state;
the ECU is configured to control the response assembly to change the state of said occupant from the first state to the second state and from the third state to the second state;
the ECU is configured to identify said occupant, create a profile of said occupant, and store information from the sensor assembly to the profile; and
the profile includes information regarding the effectiveness of the action of the response assembly for changing the state of the specific occupant associated with the profile.

20. The seat assembly of claim 19, wherein the ECU is configured to activate opposite response assembly actions when changing the state of said occupant from the first state to the second state relative to changing the state of said occupant from the third state to the second state.

* * * * *